(12) United States Patent
Haering et al.

(10) Patent No.: US 7,416,867 B2
(45) Date of Patent: Aug. 26, 2008

(54) ENZYMATIC PRODUCTION OF (METH)ACRYLIC ACID ESTERS

(75) Inventors: Dietmar Haering, Schriesheim (DE); Eva Wagner, Speyer (DE); Bernd Bruchmann, Freinsheim (DE); Erich Beck, Ladenburg (DE); Bernhard Hauer, Fussgoenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 274 days.

(21) Appl. No.: 10/545,075

(22) PCT Filed: Jan. 28, 2004

(86) PCT No.: PCT/EP2004/000700

§ 371 (c)(1),
(2), (4) Date: Aug. 9, 2005

(87) PCT Pub. No.: WO2004/076676

PCT Pub. Date: Sep. 10, 2004

(65) Prior Publication Data

US 2006/0141593 A1    Jun. 29, 2006

(30) Foreign Application Priority Data

Feb. 26, 2003    (DE) ................ 103 08 504

(51) Int. Cl.
*C12P 7/64* (2006.01)
*C12P 7/62* (2006.01)
*C12N 9/18* (2006.01)
*C12N 9/20* (2006.01)

(52) U.S. Cl. ................ 435/134; 435/135; 435/197; 435/198

(58) Field of Classification Search .......... 435/134, 435/135, 197, 198
See application file for complete search history.

(56) References Cited

U.S. PATENT DOCUMENTS 2,680,735 A    6/1954    Fegley et al.
5,240,835 A    8/1993    Pettrone et al.
6,274,357 B1 *  8/2001    Davies et al. .......... 435/134

FOREIGN PATENT DOCUMENTS

| DE | 196 47 395 | 5/1998 |
|---|---|---|
| DE | 101 18 232 | 10/2002 |
| EP | 0 999 229 | 5/2000 |
| JP | 04 292675 | 10/1992 |
| JP | 08-277245 | 10/1996 |
| JP | 2001-294554 | 10/2001 |
| JP | 2001-294555 | 10/2001 |
| WO | 00/63150 | 10/2000 |
| WO | 01/46286 | 6/2001 |

OTHER PUBLICATIONS

Tor, R. et al.: "Enzymatically catalysed transesterifications of acryl and methacryl monomeric esters", Enzyme Microb. Technol., vol. 12, No. 1, pp. 299-304, Apr. 1990. XP002138281.
Kumar, Rajesh et al.: "Biocatalytic Route to Well-Defined Macromers Built around a Sugar Core", J. Am. Chem. Soc., vol. 124, No. 9, pp. 1850-1851, Mar. 6, 2002. XP-002282214.
Kumar, Rajesh et al.: "Enzyme-Catalyzed Synthesis of Well-Defined Macromers Built around a Sugar Core", American Chemical Society, Chapter 9, vol. 840, pp. 107-118, 2003. XP008031056.
Vänttinen, Eero et al.: "Optically Active 1,3-Dioxolane-4-methanols. Lipase-Catalysed Acylation of Racemic Ketals and Diastereomeric Acetals", Tetrahedron: Asymmetry, vol. 7, No. 10, pp. 3037-3046, 1996. XP004048392.
Hajjar, Adam B. et al.: "Preparation of Monomeric Acrylic Ester Intermediates Using Lipase Catalysed Transesterifications in Organic Solvents", Biotechnology Letters, vol. 12, No. 11, pp. 825-830, 1990. XP008031024.
Mori, Hideharu et al.: "Protection and Polymeization of Functional Monomers. 21. Anionic Living Polymerization of (2,2-Dimethyl-1,3-dioxolan-4-yl)methyl Methacrylate", Macromolecules, vol. 27, pp. 35-39, 1994. XP-002282411.
Deschenaux, Robert et al.: "Transition-Metal-Catalyzed Asymmetric Organic Synthesis via Polymer-Attached Optically Active Phosphine Ligands. 13. Asymmetric Hydrogenation with Polymer Catalysts Containing Primary and Chiral Secondary Pendant Alcohols", J. Org. Chem., vol. 50, pp. 2299-2302, 1985.
De Goede, A.T.J.W. et al.: "Selective Lipase-Catalyzed Esterification of Alkyl Glycosides", Biocatalysis, vol. 9, pp. 145-155, 1994.

* cited by examiner

*Primary Examiner*—Herbert J Lilling
(74) *Attorney, Agent, or Firm*—Oblon, Spivak, McClelland, Maier & Neustadt, P.C.

(57) ABSTRACT

A method for the production of partially esterified (meth) acrylic acid esters of polyalcohols and the use thereof.

9 Claims, No Drawings

ENZYMATIC PRODUCTION OF (METH)ACRYLIC ACID ESTERS

The present invention relates to a process for preparing partial (meth)acrylic esters of polyalcohols and to their use.

(Meth)acrylic esters are generally prepared by acid- or base-catalyzed esterification of (meth)acrylic acid or transesterification of other (meth)acrylic esters with alcohols.

Partial (meth)acrylic esters generally cannot be prepared specifically by an esterification or transesterification, since statistical mixtures are obtained.

When acetal- or ketal-protected polyalcohols are being used an acid-catalyzed process for their preparation is no longer possible, since acetal and ketal groups are acid-labile.

In the case of base-catalyzed transesterification or other syntheses the products are often complex mixtures which are occasionally colored. In order to remove coloration and unconverted reactants it is necessary to work up the product mixtures by means of costly and inconvenient alkaline washes.

U.S. Pat. No. 2,680,735 describes the preparaton of (meth)acrylic esters of acetal- and ketal-protected glycerol by a transesterification of the acetal- and ketal-protected glycerol with lower (meth)acrylic esters at temperatures above 70° C. with catalysis by alkali metal oxides, sodium methoxide or sodium ethoxide.

R. Deschenaux and J. K. Stille describe the same reaction in *J. Org. Chem.*, 1985, 50, 2299-2302, using titanium tetraisopropoxide as catalyst, with subsequent acidic cleavage of the ketal protective groups.

A disadvantage of this preparation variant is the possibility of colorations of the reaction mixture when metal catalysts are used.

JP 2001-294 555 (CA No. 135:303 607) and JP 2001-294 554 (CA No. 135:303 606) describe the preparation of glyceryl monomethacrylate by reaction of methacrylic acid with glycidol (2,3-epoxy-1-propanol).

Disadvantages there are the yield of not more than 80% and the low purity of 95%.

JP 08-277 245 (CA No. 126:31792) describes the preparation of glyceryl mono-(meth)acrylate by hydrolysis of glycidyl (meth)acrylate.

A disadvantage of these synthesis routes, however, is the involvement of highly reactive and toxic epoxides.

The preparation of (meth)acrylic esters by an enzymatic esterification or transesterification is known.

Kumar and Gross describe in *J. Am. Chem. Soc.* 2002, 124, 1850-1851 the lipase-catalyzed reaction of isopropylidene-protected sugars by reaction with vinyl methacrylate. Complete reaction is achieved by means of the specific reactant, vinyl methacrylate, since vinyl alcohol liberated is withdrawn from the reaction equilibrium as acetaldehyde. A disadvantage of this process is that vinyl methacrylate is not commercially available.

A. T. J. W. de Goede et al. describe in *Biocatalysis*, 1994, 9, 145-155 the transesterification of α-O-octylglucoside with ethyl acrylate to form the 6-O-acrylic ester in the presence of lipases. Disadvantages of this process are that it is restricted to glucosides and glycosidic bonds and reacts sensitively to steric influences in the glucoside. Moreover, products with relatively high degrees of acrylicization are obtained due to unselective side reactions.

EP-A1 999 229 describes the enzymatic esterification and transesterification of polyoxyalkylenes.

Hajjar et al. describe in *Biotechnol. Lett.* 1990, 12, 825-830 the enzymatic transesterification of cyclic and open-chain alkanediols with ethyl acrylate with a lipase from *Chromobacterium viscosum*. The reactions proceed with an 18-fold molar excess of the alkyl acrylate over the diol in a solvent-free system. This produces mixtures of monoacrylates and diacrylates.

U.S. Pat. No. 5,240,835 describes the transesterification of alkyl acrylates with alcohols under catalysis by a biocatalyst from *Corynebacterium oxydans*. Exemplified therein is the reaction of a 96-fold molar excess of ethyl acrylate with 2,2-dimethyl-1,3-propanediol. The yield, after 3 days at 30° C., was only 21%.

It is an object of the present invention to provide a further process with which partial (meth)acrylic esters of polyalcohols can be prepared in high conversions and with high purities from simple reactants. The synthesis ought to proceed under mild conditions, giving products having a low color number and high purity.

We have found that this object is achieved by a process for preparing partial (meth)acrylic esters by subjecting polyalcohols (C) in which at least two hydroxyl groups together are joined in an acetal group or ketal group to esterification with (meth)acrylic acid or to transesterification with at least one (meth)acrylic ester (D) in the presence of at least one enzyme (E).

By means of the process of the invention it is possible to prepare partial (meth)acrylic esters (F) in high chemical and space/time yield and under mild conditions with good color numbers.

(Meth)acrylic acid in this text stands for methacrylic acid and acrylic acid, preferably for acrylic acid.

Polyalcohols (C) useful in accordance with the invention are those compounds which comprise at least one acetal group or ketal group, preferably from 1 to 5, more preferably from 1 to 3, very preferably 1 or 2, and in particular one acetal or ketal group, and at least one hydroxyl group (—OH), preferably from 1 to 10, more preferably from 1 to 6, very preferably from 1 to 3, in particular 1 or 2, and especially one hydroxyl group.

In the acetal groups and ketal groups of the polyalcohols (C) 2 hydroxyl groups of the polyols (B) on which the polyalcohols (C) are based are in each case joined together.

Preferred polyalcohols (C) are those obtainable by (a) reacting an aldehyde or ketone (A) with a polyol (B) and (b) where appropriate, purifying the reaction mixture obtainable from a).

Aldehydes or ketones (A) are of the formula I $$R^1\text{—C}(=\text{O})\text{—}R^2 \qquad (I),$$

where $R^1$ and $R^2$ independently of one another are hydrogen, $C_1$-$C_{18}$ alkyl, $C_2$-$C_{18}$ alkyl uninterrupted or interrupted by one or more oxygen and/or sulfur atoms and/or by one or more substituted or unsubstituted imino groups, or are $C_2$-$C_{18}$ alkenyl, $C_6$-$C_{12}$ aryl, $C_5$-$C_{12}$ cycloalkyl or a five- or six-membered, oxygen, nitrogen and/or sulfur-containing heterocycle, it being possible for the specified radicals to be substituted in each case by aryl, alkyl, aryloxy, alkyloxy, heteroatoms and/or heterocycles or for $R^1$ and $R^2$ together with the carbonyl carbon to form a four- to twelve-membered ring.

Examples of $R^1$ and/or $R^2$ are hydrogen, methyl, ethyl, iso-propyl, n-propyl, n-butyl, iso-butyl, sec-butyl, tert-butyl, n-hexyl, n-heptyl, n-octyl, n-decyl, n-dodecyl, n-tetradecyl, n-hexadecyl, n-octadecyl, 2-ethylhexyl, cyclopentyl, cyclohexyl, cyclooctyl, cyclododecyl, phenyl or naphthyl, preference being given to hydrogen, methyl, and phenyl, and particular preference to methyl.

Examples of aldehydes and ketones (A) are formaldehyde, acetaldehyde, propionaldehyde, n-butyraldehyde, isobutyraldehyde, pivaldehyde, benzaldehyde, acetone, methyl ethyl ketone, diethyl ketone, acetophenone, benzophenone, cyclopentanone, cyclohexanone or cyclododecanone, preference being given to formaldehyde, acetaldehyde, pivaldehyde, acetone, methyl ethyl, ketone, diethyl ketone, cyclopentanone or cyclohexanone, particular preference to formaldehyde, acetone or cyclopentanone, and very particular preference to acetone.

Polyols (B) are polyols having from 3 to 10 hydroxyl groups, preferably from 3 to 6.

Examples of polyols (B) are glycerol, diglycerol, trimethylolbutane, trimethylolpropane, ditrimethylolpropane, trimethylolethane, pentaerythritol, dipentaerythritol, sorbitol, mannitol, diglycerol, threitol, erythritol, adonitol (ribitol), arabitol (lyxitol), xylitol, dulcitol (galactitol), maltitol or isomalt. Preference is given to sorbitol, glycerol, diglycerol, trimethylolpropane, ditrimethylolpropane, trimethylolethane, and pentaerythritol, particular preference to glycerol, trimethylolpropane, and pentaerythritol, and very particular preference to glycerol.

The reaction of an aldehyde or ketone (A) with a polyol (B) is known per se, is not restricted, and can take place, for example, as described in Organikum, VEB Deutscher Verlag der Wissenschaften, 17th edition, Berlin 1988, p. 398.

Typically the aldehyde/ketone (A) and the polyol (B) are reacted with one another in a stoichiometry of from 0.7 to 1.2 mol (A): 2 mol hydroxyl groups in (B) that are to be protected, preferably 0.8-1.2:2, more preferably 0.9-1.1:2, very preferably 0.95-1.1:2, and in particular 1:2 mol/mol.

The reaction takes place in general at a temperature of from 0 to 120° C., in particular from 20 to 100° C., more preferably from 30 to 80° C., and very preferably from 40 to 80° C.

The reaction is generally at an end within 12 hours, preferably within from 15 minutes to 10 hours, more preferably in 30 minutes to 8 hours, very preferably from 45 minutes to 6 hours, and in particular within from 1 to 4 hours.

The acetalization/ketalization takes place in general with acid catalysis, catalyzed for example by mineral acids, such as hydrochloric acid, sulfuric acid, nitric acid, or phosphoric acid, for example, para-toluenesulfonic acid, benzenesulfonic acid, methanesulfonic acid, trifluoromethanesulfonic acid, mineral clays or acidic ion exchangers, or catalyzed by enzymes.

The reaction can be conducted without solvent or preferably in the presence of a solvent, examples being ethers and hydrocarbons, including halogenated hydrocarbons.

The acetalization/ketalization is conducted preferably with removal of the water liberated during the reaction, in the presence for example of molecular sieve or zeolites or by membrane separation, or, with particular preference, with azeotropic removal of water by a solvent which forms an azeotrope with water.

The acetalization/ketalization can take place with particular preference as described in DE-A1 196 47 395, and especially from page 2 line 55 to page 4 line 20 therein, the disclosure content of which is hereby incorporated expressly by reference.

In a further step b), if desired, the reaction mixture obtainable from a) can be purified, by means for example of filtration, distillation, rectification, chromatography, treatment with ion exchangers, adsorbents, neutral, acidic and/or alkaline washing, stripping or crystallization.

Examples of the acetal- or ketal-protected polyalcohols (C) useful in accordance with the invention are therefore those polyalcohols preparable by protecting the polyols (B) with aldehydes or ketones (A).

These are, with particular preference, polyalcohols (C) containing a 1,3-dioxolane or 1,3-dioxane structure which is monosubstituted or disubstituted in position 2, especially those containing a 2,2-dimethyl-1,3-dioxolane or 2,2-dimethyl-1,3-dioxane structure.

Particularly preferred polyalcohols (C) are 4-hydroxymethyl-2,2-dimethyl-1,3-dioxolane, 4-hydroxymethyl-2-methyl-1,3-dioxolane, 4-hydroxymethyl-2,2-diethyl-1,3-dioxolane, 4-hydroxymethyl-2-tert-butyl-1,3-dioxolane, 4-hydroxymethyl-2-phenyl-1,3-dioxolane, 5-ethyl-5-hydroxymethyl-2,2-dimethyl-1,3-dioxane, 5-ethyl-5-hydroxymethyl-2-methyl-1,3-dioxane, 5-ethyl-5-hydroxymethyl-2,2-diethyl-1,3-dioxane, 5-ethyl-5-hydroxy-methyl-2-tert-butyl-1,3-dioxane, 5-ethyl-5-hydroxymethyl-2-phenyl-1,3-dioxane, 1,2-O-isopropylidene-α-D-glucofuranose, 2,3-O-isopropylidene-threitol (=2,2-dimethyl-1,3-dioxolane-4,5-dimethanol), and 5,5-bis(hydroxymethyl)-2,2-dimethyl-1,3-dioxane. A further example is 5-ethyl-5-hydroxymethyl-1,3-dioxane.

Step c) is the esterification with (meth)acrylic acid or, preferably, the transesterification of the acetal- or ketal-protected polyalcohol (C) with at least one, preferably one, (meth)acrylate (D) in the presence of at least one, preferably one, enzyme (E) that catalyzes the transesterification.

Compounds (D) can be (meth)acrylic acid or esters of (meth)acrylic acid with a saturated alcohol, preferably saturated $C_1$-$C_{10}$ alkyl esters of (meth)acrylic acid, more preferably saturated $C_1$-$C_4$ alkyl esters of (meth)acrylic acid.

Saturated for the purposes of this text means compounds without multiple C—C bonds (except of course for the C=C double bond in the (meth)acrylic units).

Examples of compounds (D) are methyl, ethyl, n-butyl, iso-butyl, n-octyl, and 2-ethylhexyl (meth)acrylate, 1,2-ethylene glycol di- and mono(meth)acrylate, 1,4-butanediol di- and mono(meth)acrylate, 1,6-hexanediol di- and mono (meth)acrylate, trimethylolpropane tri(meth)acrylate, and pentaerythritol tetra(meth)acrylate.

Particular preference is given to methyl, ethyl, n-butyl, and 2-ethylhexyl (meth)acrylate and very particular preference to methyl, ethyl, and n-butyl (meth)acrylate.

The enzymatic esterification or transesterification with a (meth)acrylate takes place in general at from 0 to 100° C., preferably from 20 to 80° C., more preferably from 20 to 70° C., and very preferably from 20 to 60° C.

Examples of enzymes (E) useful in accordance with the invention are those selected from hydrolases (E.C. 3.-.-.-), and among these especially from the esterases (E.C. 3.1.-.-), lipases (E.C. 3.1.1.3), glycosylases (E.C. 3.2.-.-), and proteases (E.C. 3.4.-.-), in free form or in a form in which they are chemically or physically immobilized on a carrier, preferably lipases, esterases or proteases, and more preferably esterases (E.C. 3.1.-.-). Very particular preference is given to Novozyme 435 (Lipase from *Candida antarctica* B) or lipase from *Aspergillus* sp., *Aspergillus niger* sp., *Mucor* sp., *Penicillium cyclopium* sp., *Geotricum candidum* sp., *Rhizopus javanicus*, *Burkholderia* sp., *Candida* sp., *Pseudomonas* sp., or porcine pancreas, and especial preference to lipase from *Candida antarctica* B or from *Burkholderia* sp.

The enzyme content of the reaction medium is generally in the range from about 0.1 to 10% by weight, based on the sum of components (C) and (D) employed.

The reaction time depends among other things on the temperature, on the amount of the enzyme catalyst used and its activity, and on the required conversion, and also on the partly esterified alcohol. The reaction time is preferably adapted so that the conversion of all hydroxyl functions originally present in the alcohol (C) is at least 70%, preferably at least 80%, more preferably at least 90%, very preferably at least 95%, and in particular at least 97%. The time sufficient for this is generally from 1 to 48 hours, preferably from 1 to 12 hours, and more preferably from 1 to 6 hours.

The molar ratio of (meth)acrylic acid compound (D) (based on the (meth)acrylic units) to partly esterified alcohol (C) (based on hydroxyl groups) can vary within a wide range, such as in a ratio, for example, of from 100:1 to 1:1, preferably from 50:1 to 1:1, more preferably from 20:1 to 1:1, and very preferably from 10:1 to 1:1.

The reaction can proceed in organic solvents or mixtures thereof or without the addition of solvents. The batches are generally substantially free of water (i.e., less than 10%, preferably less than 5%, more preferably less than 1%, and very preferably less than 0.5% by volume of water added).

Suitable organic solvents are those known for these purposes, examples being tertiary monools, such as $C_3$-$C_6$ alcohols, preferably tert-butanol, tert-amyl alcohol, pyridine, poly-$C_1$-$C_4$ alkylene glycol di-$C_1$-$C_4$ alkyl ethers, preferably polyethylene glycol di-$C_1$-$C_4$ alkyl ethers, such as 1,2-dimethoxyethane, diethylene glycol dimethyl ether, polyethylene glycol dimethyl ether 500, $C_1$-$C_4$ alkylene carbonates, especially propylene carbonate, $C_3$-$C_6$ alkyl acetates, especially tert-butyl acetate, THF, toluene, 1,3-dioxolane, acetone, iso-butyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and single-phase or multiphase mixtures thereof. It can be advantageous to separate alcohol or water that is liberated by means of a binary or ternary heteroazeotrope which boils as close as possible to the temperature optimum of the enzyme used. The alcohol removed in this way can then be removed by phase separation or membrane vapor separation.

As an option it is possible to add aqueous solvents to the organic solvents, thereby producing single-phase or multiphase reaction solutions, depending on the organic solvent. Examples of aqueous solvents are water and also aqueous, dilute (e.g., 10 to 100 mM) buffers, with a pH for example in the range from about 6 to 8, such as potassium phosphate buffer or TRIS-HCl buffer, for example.

The water fraction in the reaction mixture is generally 0-10% by volume. The reactants are preferably used without pretreatment (drying, water doping).

The substrates are either in solution, in suspension as solids, or in emulsion in the reaction medium. The initial concentration of the reactants is preferably in the range from about 0.1 to 20 mol/l, in particular from 0.15 to 10 mol/l or from 0.2 to 5 mol/l.

The reaction can take place continuously, in a tube reactor or in a stirred reactor cascade, for example, or batchwise.

The reaction can be conducted in all reactors suitable for such reactions. Reactors of this kind are known to the skilled worker. The reaction preferably takes place in a stirred tank reactor or fixed bed reactor.

The reaction mixture can be mixed using any desired methods. There is no need for special stirring apparatus. The reaction medium can be a single phase or a plurality of phases and the reactants are dissolved, suspended or emulsified therein, charged to the reaction vessel together where appropriate with molecular sieve, and admixed with the enzyme preparation at the start of the reaction and also, where appropriate, one or more times during the course of the reaction.

The temperature during the reaction is adjusted to the desired level and can, if desired, be raised or lowered during the course of the reaction.

Where the reaction is carried out in a fixed bed reactor, said reactor is preferably packed with immobilized enzymes, the reaction mixture being pumped through a column packed with the enzyme. It is also possible to carry out the reaction in a fluidized bed, in which case the enzyme is used in a form in which it is immobilized on a carrier. The reaction mixture can be pumped continuously through the column, with the residence time and hence the desired conversion being controllable by means of the flow rate. It is also possible to pump the reaction mixture in circulation through a column, with the possibility also of distillative removal of the alcohol that is liberated at the same time, under reduced pressure.

The removal of water in the case of an esterification, or of alcohols released in a transesterification from the alkyl (meth)acrylates, takes place continuously or gradually in a manner known per se, by means of reduced pressure, azeotropic removal, absorption, pervaporation, and diffusion over membranes, for example.

Suitable for this purpose are, preferably, molecular sieves or zeolites (with a pore size, for example, in the range of about 3-10 angstroms), distillative separation or separation using appropriate semipermeable membranes.

Yet another possibility is to pass the isolated mixture of alkyl (meth)acrylate and its parent alcohol, said mixture frequently forming an azeotrope, directly to a plant for the preparation of the alkyl (meth)acrylate, so as to reuse it therein in an esterification with (meth)acrylic acid.

After the end of the reaction the reaction mixture obtainable from c) can be used further without further purification or, if required, can be purified in a further step d).

d) Generally the enzyme used is just separated off from the reaction mixture and the reaction product is freed from any organic solvent used.

The enzyme is separated off generally by filtration, absorption, centrifugation or decanting. The enzyme separated off can subsequently be used for further reactions.

Removal of the organic solvent takes place generally by distillation, rectification or, in the case of solid reaction products, by filtration.

For the further purification of the reaction product it is also possible to carry out a chromatography.

Preferably in step d), however, just the enzyme used and any solvent used are separated off.

The reaction conditions in the enzymatic esterification or transesterification are mild. The low temperatures and other mild conditions prevent the formation of by-products in step c), which might otherwise originate, for example, from chemical catalysts or as a result of unwanted free-radical polymerization of the (meth)acrylate used, which can otherwise be prevented only by adding stabilizers. In the reaction regime of the invention it is possible to add additional stabilizer to the (meth)acrylic compound (D) over and above the storage stabilizer present in any case, examples of such additional stabilizers including hydroquinone monomethyl ether, phenothiazine, phenols, such as 2-tert-butyl-4-methylphenol or 6-tert-butyl-2,4-dimethyl-phenol, for example, or N-oxyls, such as 4-hydroxy-2,2,6,6-tetramethylpiperidine-N-oxyl, and 4-oxo-2,2,6,6-tetramethylpiperidine-N-oxyl, in amounts for example of from 50 to 2000 ppm. The transesterification or esterification is advantageously conducted in the presence of an oxygenous gas, preferably air or air/nitrogen mixtures. Additionally the enzyme catalyst can be removed without problems from the end product. Additionally there is generally no substantial cleavage of the acetal groups or ketal groups by enzymatic hydrolysis; the proportion of by-products is generally less than 10%, preferably less than 5%.

The acetal- and/or ketal-protected (meth)acrylic esters obtainable from stages c) or d) can be used as such, but are preferably deprotected in a stage e) and, where appropriate, purified in a stage f).

The cleavage in stage e) generally takes place under acid catalysis and with addition of water, and is known per se and not restricted.

The reaction takes place in general at a temperature of from 20 to 150° C., in particular at from 40 to 120° C., and very preferably at from 50 to 100° C.

The reaction is generally over within 12 hours, preferably from within 15 minutes to 10 hours, more preferably in 30 minutes to 8 hours, very preferably from 45 minutes to 6 hours, and in particular within from 1 to 4 hours.

The cleavage of the acetals/ketals generally takes place under acid catalysis, catalyzed for example by mineral acids, such as hydrochloric acid, sulfuric acid, nitric acid or phosphoric acid, para-toluenesulfonic acid, benzenesulfonic acid, methanesulfonic acid, trifluoromethanesulfonic acid, mineral clays, acidic ion exchangers or catalyzed by enzymes, with the addition of up to 20%, preferably up to 15%, and more preferably up to 10% by weight of water.

The reaction can be conducted without solvent or in preferred presence of such a solvent, examples of which include ethers, alcohols, hydrocarbons, ketones, halogenated hydrocarbons, and water.

The cleavage can be conducted preferably as described in WO 00/63149, in particular from page 4 line 28 to page 18 line 24 therein and the examples, WO 00/63150, particularly from page 5 line 12 to page 16 line 30 therein and the examples, and in DE-A1 101 18 232, particularly from page 3 line 49 to page 4 line 32 therein and the examples, the disclosure content of these three publications hereby being expressly incorporated by reference.

The reaction mixture obtainable from e) can be purified if desired in a further step f), purification taking place for example by filtration, distillation, rectification, chromatography, treatment with ion exchangers, adsorbents, neutral, acidic and/or alkaline washing, stripping or crystallization.

The acetal- and/or ketal-protected (meth)acrylic esters obtainable from stages c) and d), or the partial (meth)acrylic esters (F) obtainable from steps e) and f), can be used with advantage as monomers or comonomers in poly(meth)acrylates or as reactive diluents in radiation-curable and/or dual-cure poly(meth)acrylates. Poly(meth)acrylates of this kind are suitable, for example, as binders in radiation-curable or dual-cure coating compositions. Additionally the partial (meth)acrylic esters (F) can be used in polyurethanes, such as in PU dispersions, PU foams, PU adhesives, and PU coatings, for example.

Coatings thus obtainable have very high scratch resistance, hardness, chemical resistance, elasticity, and adhesion, on both hydrophilic and hydrophobic substrates.

The present invention accordingly further provides for the use of the acetal-/ketal-protected or partial (meth)acrylic esters prepared by the process of the invention as reactive diluents or binders in radiation-curable or dual-cure coating materials, preferably in topcoats, more preferably in transparent clearcoat materials. The partial (meth)acrylic esters prepared in accordance with the invention can of course also be used as monomers in polymerizations, together where appropriate with other polymerizable monomers, such as (meth) acrylic acid, (meth)acrylic esters, styrene, butadiene, acrylonitrile, vinyl acetate, N-vinylpyrrolidone, 4-hydroxybutyl vinyl ether or N-vinylformamide, for example.

"Dual cure" means that the coating materials are curable thermally and with actinic radiation. Actinic radiation for the purposes of the present invention means electromagnetic radiation such as visible light, UV radiation or X-rays, especially UV radiation, and corpuscular radiation such as electron beams.

Radiation-curable binders are those which can be cured by means of actinic radiation as defined above, in particular by means of UV radiation.

The present invention further provides coating formulations comprising the acetal-/ketal-protected or partial (meth) acrylic esters obtainable by the process of the invention. The partial (meth)acrylic esters can be used both in basecoat and in topcoat materials. In view of their particular properties, such as the raising of the scratch resistance and elasticity, and the lowering of the viscosity, particularly in the case of branched polyacrylates, of a radiation-cured clearcoat, their use in topcoats is preferred.

Besides the partial (meth)acrylic esters (F) obtainable by the process of the invention a radiation-curable composition of the invention may comprise the following components:

(G) at least one polymerizable compound having two or more copolymerizable, ethylenically unsaturated groups, (H) if desired, reactive diluents, (I) if desired, photoinitiator, and (J) if desired, further, typical coatings additives.

Suitable compounds (G) include radiation-curable, free-radically polymerizable compounds having a plurality of, i.e., at least two, copolymerizable, ethylenically unsaturated groups.

Compounds (G) are preferably vinyl ether compounds or (meth)acrylate compounds, particular preference being given in each case to the acrylate compounds, i.e., to the derivatives of acrylic acid.

Preferred vinyl ether and (meth)acrylate compounds (G) contain from 2 to 20, preferably from 2 to 10, and very preferably from 2 to 6 copolymerizable, ethylenically unsaturated double bonds.

Particular preference is given to such compounds (G) having an ethylenically unsaturated double bond content of 0.1-0.7 mol/100 g, very preferably 0.2-0.6 mol/100 g.

The number-average molecular weight $M_n$ of the compounds (G), unless otherwise specified, is preferably below 15 000, more preferably 300-12 000, very preferably from 400 to 5000, and in particular 500-3000 g/mol (as determined by gel permeation chromatography using polystyrene standards and tetrahydrofuran as eluent).

As (meth)acrylate compounds mention may be made of (meth)acrylic esters and especially acrylic esters and also of vinyl ethers of polyfunctional alcohols, especially those which other than the hydroxyl groups comprise no functional groups or, if any at all, contain ether groups. Examples of such alcohols include bifunctional alcohols, such as ethylene glycol, propylene glycol and their counterparts with higher degrees of condensation, such as diethylene glycol, triethylene glycol, dipropylene glycol, tripropylene glycol etc., 1,2-, 1,3- or 1,4-butanediol, 1,5-pentanediol, 1,6-hexanediol, 3-methyl-1,5-pentanediol, neopentyl glycol, alkoxylated phenolic compounds, such as ethoxylated and/or propoxylated bisphenols, 1,2-, 1,3- or 1,4-cyclohexanedimethanol, alcohols with a functionality of three or more, such as glycerol, trimethylolpropane, butanetriol, trimethylolethane, pentaerythritol, ditrimethylolpropane, dipentaerythritol, sorbitol, mannitol, and the corresponding alkoxylated alcohols, especially ethoxylated and/or propoxylated alcohols.

The alkoxylation products are obtainable conventionally by reacting the above alcohols with alkylene oxides, especially ethylene oxide or propylene oxide. The degree of alkoxylation per hydroxyl group is preferably from 0 to 10, i.e., 1 mol of hydroxyl group may have been alkoxylated with up to 10 mol of alkylene oxides.

As (meth)acrylate compounds mention may further be made of polyester (meth)acrylates, which are the (meth) acrylic esters or vinyl ethers of polyesterols, and also of urethane, epoxy or melamine (meth)acrylates.

Urethane (meth)acrylates, for example, are obtainable by reacting polyisocyanates with hydroxyalkyl (meth)acrylates and, where appropriate, chain extenders such as diols, polyols, diamines, polyamines, or dithiols or polythiols.

The urethane (meth)acrylates preferably have a number-average molar weight $M_n$ of from 500 to 20 000, in particular from 750 to 10 000, and more preferably from 750 to 3000 g/mol (as determined by gel permeation chromatography using polystyrene standards).

The urethane (meth)acrylates preferably comprise from 1 to 5, more preferably from 2 to 4, mol of (meth)acrylic groups per 1000 g of urethane (meth)acrylate.

Epoxy (meth)acrylates are obtainable by reacting epoxides with (meth)acrylic acid. Examples of suitable epoxides include epoxidized olefins or glycidyl ethers, e.g. bisphenol A diglycidyl ether or aliphatic glycidyl ethers, such as butanediol diglycidyl ether.

Melamine (meth)acrylates are obtainable by reacting melamine with (meth)acrylic acid or the esters thereof.

The epoxy (meth)acrylates and melamine (meth)acrylates preferably have a number-average molar weight $M_n$ of from 500 to 20 000, more preferably from 750 to 10 000 g/mol and very preferably from 750 to 3000 g/mol; the amount of (meth) acrylic groups is preferably from 1 to 5, more preferably from 2 to 4, per 1000 g of epoxy (meth)acrylate or melamine (meth)acrylate (as determined by gel permeation chromatography using polystyrene standards and tetrahydrofuran as eluent).

Also suitable are carbonate (meth)acrylates, comprising on average preferably from 1 to 5, in particular from 2 to 4, more preferably 2 or 3 (meth)acrylic groups and, with very particular preference, 2 (meth)acrylic groups.

The number-average molecular weight $M_n$ of the carbonate (meth)acrylates is preferably less than 3000 g/mol, more preferably less than 1500 g/mol, very preferably less than 800 g/mol (as determined by gel permeation chromatography using polystyrene standards and tetrahydrofuran as mobile phase).

The carbonate (meth)acrylates are readily obtainable by transesterification of carbonic esters with polyhydric, preferably dihydric, alcohols (diols, e.g. hexanediol) and subsequent esterification of the free OH groups with (meth)acrylic acid or else transesterification with (meth)acrylic esters, as described for example in EP-A 92 269. They are also obtainable by reacting phosgene, urea derivatives with polyhydric alcohols, e.g. dihydric alcohols.

Suitable reactive diluents (compounds (H)) include radiation-curable, free-radically or cationically polymerizable compounds having only one ethylenically unsaturated co-polymerizable group.

Examples that may be mentioned include $C_1$-$C_{20}$ alkyl (meth)acrylates, vinylaromatics having up to 20 carbon atoms, vinyl esters of carboxylic acids comprising up to 20 carbon atoms, ethylenically unsaturated nitriles, vinyl ethers of alcohols comprising 1 to 10 carbon atoms, α,β-unsaturated carboxylic acids and their anhydrides, and aliphatic hydrocarbons having from 2 to 8 carbon atoms and 1 or 2 double bonds.

Preferred alkyl (meth)acrylates are those with a $C_1$-$C_{10}$ alkyl radical, such as methyl methacrylate, methyl acrylate, n-butyl acrylate, ethyl acrylate, and 2-ethylhexyl acrylate.

In particular, mixtures of the alkyl (meth)acrylates are also suitable.

Examples of vinyl esters of carboxylic acids having 1 to 20 carbon atoms are vinyl laurate, vinyl stearate, vinyl propionate, and vinyl acetate.

Examples of α,β-unsaturated carboxylic acids and their anhydrides include acrylic acid, methacrylic acid, fumaric acid, crotonic acid, itaconic acid, maleic acid, and maleic anhydride, preferably acrylic acid.

Examples of suitable vinylaromatic compounds include vinyltoluene, α-butylstyrene, 4-n-butylstyrene, 4-n-decylstyrene, and, preferably, styrene.

Examples of nitriles are acrylonitrile and methacrylonitrile.

Examples of suitable vinyl ethers include vinyl methyl ether, vinyl isobutyl ether, vinyl hexyl ether, and vinyl octyl ether.

As nonaromatic hydrocarbons having 2 to 8 carbon atoms and one or two olefinic double bonds mention may be made of butadiene, isoprene, and of ethylene, propylene, and isobutylene.

It is further possible to employ N-vinylformamide, N-vinylpyrrolidone, and N-vinylcaprolactam.

As photoinitiator (I) it is possible to use photoinitiators known to the skilled worker, examples being those in "Advances in Polymer Science", Volume 14, Springer Berlin 1974 or in K. K. Dietliker, Chemistry and Technology of UV- and EB-Formulation for Coatings, Inks and Paints, Volume 3; Photoinitiators for Free Radical and Cationic Polymerization, P. K. T. Oldring (ed.), SITA Technology Ltd, London.

Suitable examples include mono- or bisacylphosphine oxides such as Irgacure 819 (bis(2,4,6-trimethylbenzoyl)phenylphosphine oxide), as described for example in EP-A 7 508, EP-A 57 474, DE-A 196 18 720, EP-A 495 751 or EP-A 615 980, examples being 2,4,6-trimethylbenzoyidiphenylphosphine oxide (Lucirin® TPO), ethyl 2,4,6-trimethylbenzoylphenylphosphinate, benzophenones, hydroxyacetophenones, phenylglyoxylic acid and derivatives thereof, or mixtures of these photoinitiators.

Examples that may be mentioned include benzophenone, acetophenone, acetonaphthoquinone, methyl ethyl ketone, valerophenone, hexanophenone, α-phenylbutyrophenone, p-morpholinopropiophenone, dibenzosuberone, 4-morpholinobenzophenone, 4-morpholinodeoxybenzoin, p-diacetylbenzene, 4-aminobenzophenone, 4'-methoxyacetophenone, β-methylanthraquinone, tert-butylanthraquinone, anthraquinonecarboxylic esters, benzaldehyde, α-tetralone, 9-acetylphenanthrene, 2-acetylphenanthrene, 10-thioxanthenone, 3-acetylphenanthrene, 3-acetylindole, 9-fluorenone, 1-indanone, 1,3,4-triacetylbenzene, thioxanthen-9-one, xanthen-9-one, 2,4-dimethylthioxanthone, 2,4-diethylthioxanthone, 2,4-diisopropylthioxanthone, 2,4dichlorothioxanthone, benzoin, benzoin isobutyl ether, chloroxanthenone, benzoin tetrahydropyranyl ether, benzoin methyl ether, benzoin ethyl ether, benzoin butyl ether, benzoin isopropyl ether, 7H-benzoin methyl ether, benz[de]anthracen-7-one, 1-naphthaldehyde, 4,4'-bis(dimethylamino) benzophenone, 4-phenylbenzophenone, 4-chlorobenzophenone, Michler's ketone, 1-acetonaphthone, 2-acetonaphthone, 1-benzoylcyclohexan-1-ol, 2-hydroxy-2,2-dimethylacetophenone, 2,2-dimethoxy-2-phenylacetophenone, 2,2-diethoxy-2-phenylacetophenone, 1,1-dichloroacetophenone, 1-hydroxyacetophenone, acetophenone dimethyl ketal, o-methoxybenzophenone, triphenylphosphine, tri-o-tolylphosphine, benz[a]anthracene-7,12-dione, 2,2-diethoxyacetophenone, benzil ketals, such as benzil dimethyl ketal, 2-methyl-1-[4-(methylthio)phenyl]-2-morpholinopropan-1-one, anthraquinones such as 2-methylanthraquinone, 2-ethylanthraquinone, 2-tert-butylanthraquinone, 1-chloroanthraquinone, 2-amylanthraquinone, and 2,3-butanedione.

Also suitable are nonyellowing or low-yellowing photoinitiators of the phenylglyoxalic ester type, as described in DE-A 198 26 712, DE-A 199 13 353 or WO 98/33761.

Among said photoinitiators phosphine oxides, α-hydroxy ketones and benzophenones are preferred.

In particular it is also possible to use mixtures of different photoinitiators.

The photoinitiators can be used alone or in combination with a photopolymerization promoter, of the benzoic acid, amine or similar type, for example.

As further, typical coatings additives (J) it is possible to make use, for example, of anti-oxidants, oxidation inhibitors, stabilizers, activators (accelerators), fillers, pigments, dyes, devolatilizers, luster agents, antistats, flame retardants, thickeners, thixotropic agents, leveling assistants, binders, antifoams, fragrances, surfactants, viscosity modifiers, plasticizers, tackifying resins (tackifiers), chelating agents or compatibilizers.

Examples of accelerators for thermo aftercure that can be used include tin octoate, zinc octoate, dibutyltin laurate, and diazabicyclo[2.2.2]octane.

It is also possible to add one or more photochemically and/or thermally activatable initiators, such as potassium peroxodisulfate, dibenzoyl peroxide, cyclohexanone peroxide, di-tert-butyl peroxide, azobisisobutyronitrile, cyclohexylsulfonyl acetyl peroxide, diisopropyl percarbonate, tert-butyl peroctoate or benzpinacol, and also, for example, those thermally activatable initiators which have a half-life at 80° C. of more than 100 hours, such as di-t-butyl peroxide, cumene hydroperoxide, dicumyl peroxide, t-butyl perbenzoate, silylated pinacols, available commercially, for example, under the trade name ADDID 600 from Wacker, or hydroxyl-containing amine N-oxides, such as 2,2,6,6-tetramethylpiperidine-N-oxyl, 4-hydroxy-2,2,6,6-tetramethylpiperidine-N-oxyl etc.

Further examples of suitable initiators are described in "Polymer Handbook", 2nd ed., Wiley & Sons, New York.

Suitable thickeners besides free-radically (co)polymerized (co)polymers include customary organic and inorganic thickeners such as hydroxymethylcellulose or bentonites.

Examples of chelating agents which can be used include ethylenediamineacetic acid and salts thereof and also α-diketones.

Suitable fillers include silicates, examples being silicates obtainable by hydrolysis of silicon tetrachloride such as Aerosil® from Degussa, silicious earth, talc, aluminum silicates, magnesium silicates, calcium carbonates, etc.

Suitable stabilizers include typical UV absorbers such as oxanilides, triazines, and benzotriazole (the latter obtainable as Tinuvin® grades from Ciba-Spezialitätenchemie), and benzophenones. They can be used alone or together with suitable free-radical scavengers, examples being sterically hindered amines such as 2,2,6,6-tetramethylpiperidine, 2,6-di-tert-butylpiperidine or derivatives thereof, e.g., bis(2,2,6,6-tetramethyl-4-piperidyl) sebacate. Stabilizers are normally used in amounts of from 0.1 to 5.0% by weight, based on the solid components present in the formulation.

Examples of stabilizers which are additionally suitable include N-oxyls, such as 4-hydroxy-2,2,6,6-tetramethylpiperidine-N-oxyl, 4-oxo-2,2,6,6-tetramethylpiperidine-N-oxyl, 4-acetoxy-2,2,6,6-tetramethylpiperidine-N-oxyl, 2,2,6,6-tetramethylpiperidine-N-oxyl, 4,4',4"-tris(2,2,6,6-tetramethylpiperidine-N-oxyl) phosphite or 3-oxo-2,2,5,5-tetra-methylpyrrolidine-N-oxyl, phenols and naphthols, such as p-aminophenol, p-nitrosophenol, 2-tert-butylphenol, 4-tert-butylphenol, 2,4-di-tert-butylphenol, 2-methyl-4-tert-butylphenol, 4-methyl-2,6-tert-butylphenol (2,6-tert-butyl-p-cresol) or 4-tert-butyl-2,6-dimethylphenol, quinones, such as hydroquinone or hydroquinone monomethyl ether, aromatic amines, such as N,N-diphenylamine, N-nitrosodiphenylamine, phenylenediamines, such as N,N'-dialkyl-paraphenylenediamine, where the alkyl radicals can be identical or different, consist independently of 1 to 4 carbon atoms, and be straight-chain or branched, hydroxylamines, such as N,N-diethylhydroxylamine, urea derivatives, such as urea or thiourea, phosphorus compounds, such as triphenyl-phosphine, triphenyl phosphite or triethyl phosphite, or sulfur compounds, such as di-phenyl sulfide or phenothiazine, for example.

Examples of typical compositions for radiation-curable materials are:
(F) 20-100%, preferably 40-90%, more preferably 50-90%, and in particular 60-80% by weight,
(G) 0-60%, preferably 5-50%, more preferably 10-40%, and in partcular 10-30% by weight,
(H) 0-50%, preferably 5-40%, more preferably 6-30%, and in particular 10-30% by weight,
(I) 0-20%, preferably 0.5-15%, more preferably 1-10%, and in partcular 2-5% by weight, and
(J) 0-50%, preferably 2-40%, more preferably 3-30%, and in particular 5-20% by weight,
with the proviso that (F), (G), (H), (I), and (J) together make 100% by weight.

The substrates are coated in accordance with methods which are conventional and are known to the skilled worker, applying at least one coating material to the target substrate in the desired thickness and removing any volatile constituents present in the coating material, with heating where appropriate. This operation can be repeated one or more times as desired. Application to the substrate may be made in a known way, for example, by spraying, troweling, knifecoating, brushing, rolling, roller coating, flow coating, laminating, injection backmolding or coextrusion. The coating thickness is generally in a range from about 3 to 1000 g/m² and preferably from 10 to 200 g/m².

Further disclosed is a method of coating substrates which comprises applying the coating material to the substrate and drying it where appropriate, curing it with electron beams or by UV exposure under an oxygenous atmosphere or, preferably, under inert gas, treating it thermally, if desired, at temperatures up to the level of the drying temperature, and then treating it thermally at temperatures of up to 160° C., preferably between 60 and 160° C.

The method of coating substrates may also be conducted by following the application of the coating material first with thermal treatment at temperatures of up to 160° C., preferably between 60 and 160° C., and then with curing using electron beams or by UV exposure under oxygen or, preferably, under inert gas.

Curing of the films formed on the substrate may take place by means of heat alone if desired. Generally, however, the coatings are cured both by exposure to high-energy radiation and thermally.

In addition to or instead of the thermal cure, curing may also take place by means of NIR radiation, which refers here to electromagnetic radiation in the wavelength range from 760 nm to 2.5 μm, preferably from 900 to 1500 nm.

Where two or more films of the coating composition are applied atop one another, it is possible for each coating operation to be followed by a thermal, NIR and/or radiation cure.

Examples of suitable radiation sources for the radiation cure include low-pressure, medium-pressure, and high-pressure mercury lamps, fluorescent tubes, pulsed lamps, metal halide lamps, electronic flash installations, which allow radiation curing without photoinitiator, or excimer sources. Radiation curing is accomplished by exposure to high-energy radiation, i.e., UV radiation or daylight, preferably light in the wavelength ($\lambda$) range of from 200 to 700 nm, more preferably from 200 to 500 nm, and very preferably from 250 to 400 nm, or by bombardment with high-energy electrons (electron beams; 150 to 300 keV). Examples of radiation sources used include high-pressure mercury vapor lamps, lasers, pulsed lamps (flash light), halogen lamps, or excimer sources. The radiation dose normally sufficient for crosslinking in the case of UV curing is in the range from 80 to 3000 mJ/cm$^2$.

It is of course also possible to use two or more radiation sources for the cure, e.g., from two to four.

These sources may also each emit in different wavelength regions.

Irradiation can be carried out where appropriate in the absence of oxygen as well, such as under an inert gas atmosphere, for example. Suitable inert gases include, preferably, nitrogen, noble gases, carbon dioxide or combustion gases. Irradiation may also take place with the coating material covered with transparent media. Examples of transparent media include polymeric films, glass or liquids, such as water. Particular preference is given to irradiation in the manner described in DE-A1 199 57 900.

The invention further provides a method of coating substrates which comprises i) coating a substrate with a coating material as described above,
ii) removing volatile constituents of the coating material, for the purpose of forming a film, under conditions in which the photoinitiator (I) essentially as yet does not form any free radicals,
iii) if desired, irradiating the film formed in step ii) with high-energy radiation, the film being precured, and then, where appropriate, machining the article coated with the precured film or contacting the surface of the precured film with another substrate,
iv) fully curing the film, thermally or with NIR radiation.

Steps iv) and iii) can also be carried out in reverse order, i.e., the film can be cured first thermally or by NIR radiation and then with high-energy radiation.

The present invention further provides substrates coated with a multicoat paint system of the invention.

The thickness of such a film to be cured as described can be from 0.1 µm up to several mm, preferably from 1 to 2000 µm, more preferably from 5 to 1000 µm, very preferably from 10 to 500 µm, and in particular from 10 to 250 µm.

The coating materials of the invention are suitable with particular preference as or in exterior coatings, i.e., those applications which are exposed to daylight, preferably on buildings or parts of buildings, interior coatings, traffic markings, and coatings on vehicles and aircraft. The coatings are employed in particular as wood, paper or plastics coatings, for woodblock flooring or furniture for example.

The process of the invention allows the preparation of partial (meth)acrylic esters (F) in high chemical and space/time yield and under mild conditions and with good color numbers. Through the use of protective groups the desired partially esterified products are obtained in a targeted way and are free from by-products.

The examples which follow are intended to illustrate the qualities of the invention without, however, restricting it.

EXAMPLES

Parts in this document, unless specified otherwise, are to be understood as referring to parts by weight.

Example 1

Isopropylidene-glycerol+ethyl acrylate (variation of solvent)

5 mmol of 2,3-isopropylidene-glycerol, 50 mmol of ethyl acrylate, 10 ml of solvent and 100 mg of Novozym 435 were shaken at 40° C. for 24 h.

The reaction mixture was filtered and the conversion to 2,3-isopropylidene-glycerol monoacrylate was determined by gas chromatography.

| Solvent | Conversion [%] |
|---|---|
| none | 74 |
| acetone | 68 |
| 1,4-dioxane | 74 |
| MTBE | 74 |
| toluene | 74 |
| acetonitrile | 74 |
| THF | 71 |

MTBE: methyl tert-butyl ether

MTBE: methyl tert-butyl ether

Example 2

Isopropylidene-glycerol+alkyl acrylate (variation of alkyl acrylate)

5 mmol of 2,3-isopropylidene-glycerol (IPG), 25-100 mmol of alkyl acrylate and 100 mg of Novozym 435 were shaken at 20, 40 or 60° C. for 24 h.

The reaction mixture was filtered and the conversion to 2,3-isopropylidene-glycerol monoacrylate was determined by gas chromatography.

| Acrylate:IPG [mol/mol] | Conversion [%] with methyl acrylate | Conversion [%] with ethyl acrylate | Conversion [%] with butyl acrylate |
|---|---|---|---|
| at 20° C. | | | |
| 5:1 | 58 | 65 | 61 |
| 7:1 | 61 | 69 | 67 |
| 10:1 | 67 | 74 | 71 |
| 10:1 (72 h) | 67 | 74 | 71 |
| 20:1 | 76 | 83 | 80 |
| at 40° C. | | | |
| 5:1 | 60 | 66 | 64 |
| 10:1 | 71 | 76 | 75 |
| 10:1 (72 h) | 69 | 75 | 73 |
| 20:1 | 79 | 85 | 84 |
| at 60° C. | | | |
| 5:1 | 61 | 67 | 66 |
| 10:1 | 72 | 78 | 76 |
| 10:1 (72 h) | 72 | 78 | 77 |
| 20:1 | 81 | 86 | 85 |

Example 3

Isopropylidene-glycerol+methyl acrylate

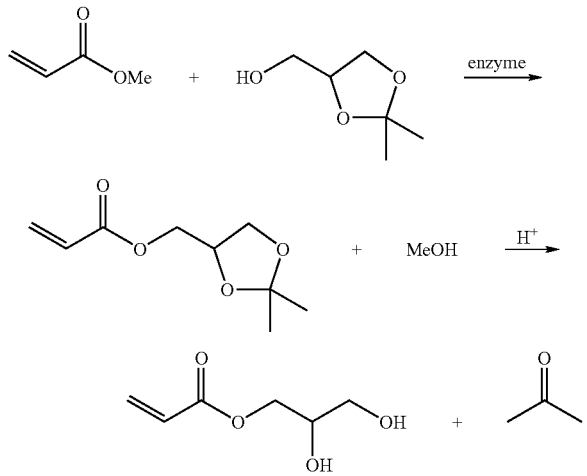

4.0 mol (528.8 g) of 2,3-isopropylidene-glycerol, 20.0 mol (1722 g) of methyl acrylate, 86 mg of phenothiazine, 344 mg of p-methoxyphenol, 800 g of molecular sieve (5 Å) and 80.0 g of Novozym 435 were stirred at room temperature for 24 h in a round-bottomed flask.

The reaction mixture was filtered and the excess methyl acrylate was removed on a rotary evaporator. The batch was run twice with reproducible conversions.

| Batch | Conversion [%] | Yield [g] |
| --- | --- | --- |
| A | 93 | 674.6 |
| B | 94 | 724.1 |

For the hydrolysis of the isopropylidene group, 680 g of 2,3-isopropylidene-glycerol monoacrylate were stirred with 680 g of water and 68 g of strongly acidic ion exchanger (Dowex 50 Wx8H$^+$ form) at room temperature for 24 h. The ion exchanger was removed by filtration and the acetone formed was removed under reduced pressure on a rotary evaporator at 20-30° C.

The resultant aqueous solution of glycerol monoacrylate can be used further directly for the copolymerization. According to the analysis by GC the organic fractions of the solution are composed of 94.3% glycerol monoacrylate, 5.2% glycerol, and 0.5% 2,3-isopropylidene-glycerol monoacryate.

As an alternative it is possible to prepare an anhydrous product by extracting the aqueous solution with ethyl acetate, drying the extract over sodium sulfate, and freeing it from ethyl acetate again on a rotary evaporator. The anhydrous, colorless oil is composed according to analysis by GC of 97.1% glycerol monoacrylate, 1.9% glycerol, 0.6% 2,3-isopropylidene-glycerol monoacrylate, and 0.3% 2,3-isopropylidene-glycerol.

Example 4

2,3-Isopropylidene-glycerol+methyl acrylate

In a round-bottomed flask 0.1 mol (13.2 g) of 2,3-isopropylidene-glycerol, 1 mol (86.1 g) of methyl acrylate and 650 mg of Novozym 435 were stirred at 60° C. under reduced pressure (450-470 mbar). The vapor (methyl acrylate+methanol) was passed in a tube into a condenser. The condensate dripped back into the reaction mixture via a dropping funnel filled with 20 g of molecular sieve (5 Å). After 6 h a sample was taken from the mixture and the conversion was determined by means of GC to 99.5%.

Example 5

2,3-Isopropylidene-glycerol+methyl methacrylate 5 mmol of 2,3-isopropylidene-glycerol (IPG), 10-50 mmol of methyl methacrylate (MMA), 1.0 g of molecular sieve (5 Å) and 100 mg of Novozym 435 were shaken at 20 or 40° C. for 24 h.

The reaction mixture was filtered and the conversion to 2,3-isopropylidene-glycerol monomethacrylate was determined by gas chromatography.

| MMA:IPG [mol:mol] | Conversion [%] at 20° C. | Conversion [%] at 40° C. |
| --- | --- | --- |
| 2:1 | 78 | 91 |
| 3:1 | 78 | 89 |
| 5:1 | 90 | 90 |
| 7:1 | 92 | 94 |
| 10:1 | 91 | 95 |

Example 6

Isopropylidene-protected trimethylolpropane+methyl acrylate

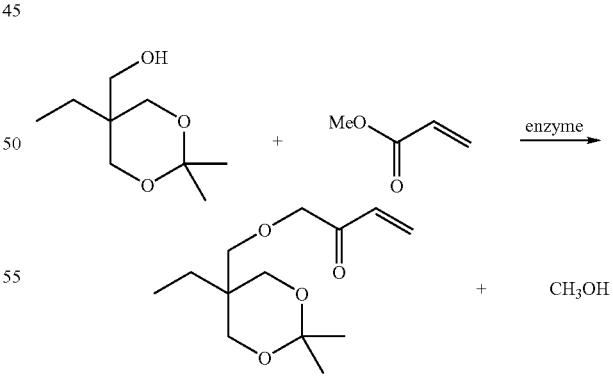

5 mmol of isopropylidene-trimethylolpropane (IPT), 10-50 mmol of methyl acrylate (MA), 1.0 g of molecular sieve (5 Å), optionally 10 ml of methyl tert-butyl ether (MTBE) and 100 mg of Novozym 435 were shaken at 20, 40 or 60° C. for 24 or 72 h. The reaction mixture was filtered and the conversion to isopropylidene-trimethylolpropane monoacrylate was determined by gas chromatography.

| MA:IPT [mol:mol] | Conversion [%] at 20° C. | Conversion [%] at 40° C. | Conversion [%] at 60° C. |
|---|---|---|---|
| Reactions without MTBE | | | |
| 2:1 (24 h) | 14 | 20 | 19 |
| 5:1 (24 h) | 14 | 16 | 22 |
| 10:1 (24 h) | 11 | 16 | 16 |
| 10:1 (72 h) | 14 | 21 | — |

| MA:IPT [mol:mol] | Conversion [%] at 20° C. | Conversion [%] at 40° C. |
|---|---|---|
| Reactions with MTBE | | |
| 2:1 (24 h) | 10 | 21 |
| 5:1 (24 h) | 11 | 19 |
| 10:1 (24 h) | 9 | 17 |
| 10:1 (72 h) | 8 | 21 |

Example 7

Isopropylidene-glucofuranose+methyl acrylate

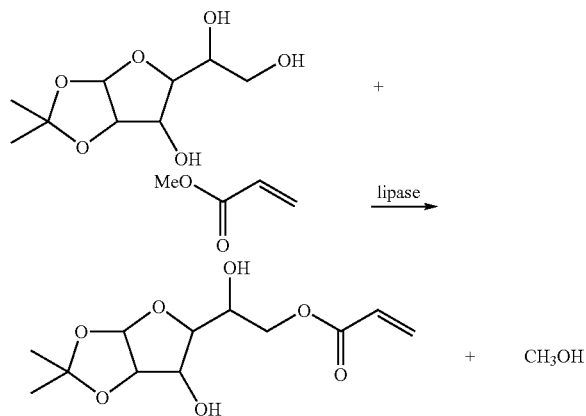

5 mmol of isopropylidene-glucofuranose (IP-Glu), 50 mmol of methyl acrylate (MA), optionally 1.0 g of molecular sieve (5 Å), optionally 10 ml of solvent, and 100 mg of Novozym 435 were shaken at 40° C. for 24 h.

The reaction mixture was filtered and the conversion to isopropylidene-glucofuranose monoacrylate was determined by gas chromatography.

| Solvent | Conversion [%] without molecular sieve | Conversion [%] with molecular sieve |
|---|---|---|
| none | 53 | 85 |
| Acetone | 51 | 73 |
| 1,4-dioxane | 54 | 80 |
| THF | 52 | 68 |

We claim:

1. An enzymatic method for preparing (meth)acrylic esters of polyalcohols comprising at least one selected from the group consisting of:
   esterifying a (meth)acrylic acid with a protected polyalcohol in the presence of at least one enzyme, and
   transesterifying at least one (meth)acrylic ester of a saturated alcohol with a protected polyalcohol in the presence of at least one enzyme;
   wherein
   the protected polyalcohol is a polyalcohol wherein at least two hydroxyl groups are joined in an acetal or ketal group, and
   at least 70% of all hydroxyl groups of the protected polyalcohol are converted to (meth)acrylic ester of protected polyalcohol.

2. The process according to claim 1, wherein the at least one (meth)acrylic ester of a saturated alcohol is a saturated $C_1$-$C_{10}$-alkyl (meth)acrylate.

3. The process according to claim 1, wherein the the protected polyalcohol is obtained by
   a) reacting an aldehyde or ketone with a polyalcohol and
   b) optionally, purifying the reaction mixture obtained from a), wherein
   the aldehyde or ketone is represented by the formula I $$R^1\text{—}C(=O)\text{—}R^2 \qquad (I),$$

where
radicals $R^1$ and $R^2$ independently of one another are hydrogen, $C_1$-$C_{18}$ alkyl, $C_2$-$C_{18}$ alkyl uninterrupted or interrupted by one or more oxygen and/or sulfur atoms and/or by one or more substituted or unsubstituted imino groups, or are $C_2$-$C_{18}$ alkenyl, $C_6$-$C_{12}$ aryl, $C_5$-$C_{12}$ cycloalkyl or a five- or six-membered, oxygen-, nitrogen- and/or sulfur-containing heterocycle, and wherein the specified radicals may be substituted in each case by aryl, alkyl, aryloxy, alkyloxy, heteroatoms and/or heterocycles or for $R^1$ and $R^2$ together with the carbonyl carbon to form a four- to twelve-membered ring,
and the polyalcohol has from 3 to 10 hydroxyl groups.

4. The process according to claim 1, wherein the protected polyalcohol comprises a 1,3-dioxolane or 1,3-dioxane structure which is mono- or disubstituted in position 2.

5. The process according to claim 4, wherein the the protected polyalcohol is at least one selected from the group consisting of 4-hydroxymethyl-2,2-dimethyl-1,3-dioxolane, 4-hydroxymethyl-2-methyl-1,3-dioxolane, 4-hydroxymethyl-2,2-diethyl-1,3-dioxolane, 4-hydroxymethyl-2-tert-butyl-1,3-dioxolane, 4-hydroxymethyl-2-phenyl-1,3-dioxolane, 5-ethyl-5-hydroxymethyl-2,2-dimethyl-1,3-dioxane, 5-ethyl-5-hydroxymethyl-2-methyl-1,3-dioxane, 5-ethyl-5-hydroxymethyl-2,2-diethyl-1,3-dioxane, 5-ethyl-5-hydroxymethyl-2-tert-butyl-1,3-dioxane, 5-ethyl-5-hydroxymethyl-2-phenyl-1,3-dioxane, 1,2-O-isopropylidene-α-D-glucofuranose, 2,3-O-isopropylidene-threitol (=2,2-dimethyl-1,3-dioxolane-4,5-dimethanol), 5,5-bis(hydroxymethyl)-2,2-dimethyl-1,3-dioxane and mixtures thereof.

6. The process according to claim 1, wherein the reaction mixture from the esterifying or the transesterifying is purified.

7. The process according to claim 1, wherein the reaction mixture from the esterifying or the transesterifying is deprotected and, optionally, purified.

8. The process according to claim 1, wherein the enzyme is at least one selected from the group consisting of esterases (E.C. 3.1.-.-), lipases (E.C. 3.1.1.3), glycosylases (E.C. 3.2.-.-), and proteases (E.C. 3.4.-.-).

9. The process according to claim 6, wherein the purified reaction mixture from the esterifying or the transesterifying is deprotected and, optionally, further purified.

* * * * *